United States Patent [19]

Dannelly

[11] 4,245,432
[45] Jan. 20, 1981

[54] SEED COATINGS

[75] Inventor: Clarence C. Dannelly, Kingsport, Tenn.

[73] Assignee: Eastman Kodak Company, Rochester, N.Y.

[21] Appl. No.: 60,546

[22] Filed: Jul. 25, 1979

[51] Int. Cl.³ .............................................. A01C 1/06
[52] U.S. Cl. ................................................. 47/57.6
[58] Field of Search .................... 47/57.6, 58, DIG. 9; 260/32.6 N

[56] References Cited

U.S. PATENT DOCUMENTS

| | | | |
|---|---|---|---|
| 3,707,807 | 1/1973 | Graves | 47/57.6 |
| 3,905,152 | 9/1975 | Loperfido | 47/57.6 |
| 3,947,996 | 4/1976 | Watts | 47/57.6 |
| 3,950,891 | 4/1976 | Hinkes | 47/57.6 |

FOREIGN PATENT DOCUMENTS 2731203  1/1979  Fed. Rep. of Germany ............ 47/57.6

*Primary Examiner*—Robert E. Bagwill
*Attorney, Agent, or Firm*—John F. Stevens; Daniel B. Reece, III

[57] ABSTRACT

Disclosed are plant seed coating compositions comprising water insoluble but water sensitive polyelectrolyte complexes. The polyelectrolyte complexes, which are formed by combining an acidic polymer with a basic polymer, provide protection for the seeds and may be used as a carrier for materials such as fertilizers, herbicides, pesticides, etc. An important feature is the fact that the polyelectrolyte complex does not dissolve when contacted with water. Instead, it swells and falls away, thereby disrupting the coating, and the swelling and falling away continue until the coating is removed. An advantage of such a coating is that there is no dissolved material available to fill the pores of the seeds to thereby retard germination. The coating quickly disintegrates upon contact with water for releasing any carried substances and exposes the seeds to their natural environment.

13 Claims, 5 Drawing Figures

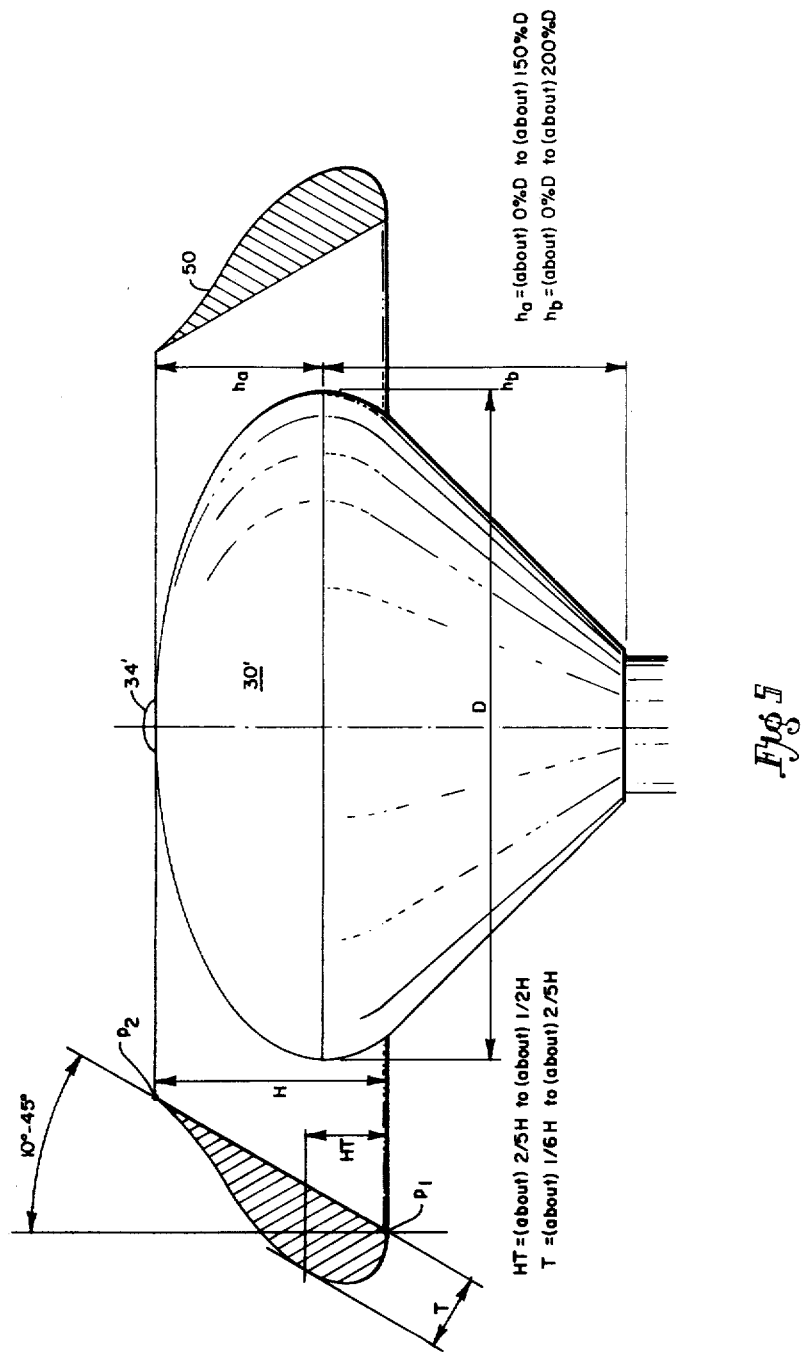

SEED COATINGS

BACKGROUND OF THE INVENTION

1. Field of the Invention

This invention relates to coating plant seeds with a functional material which disintegrates after becomming wet to allow normal germination of the seeds.

2. Description of the Prior Art

It is known in the art to coat seeds with a functional material to provide protection against mechanical or environmental damage, and to use such coatings as a carrier for various materials such as, for example, fertilizer, pesticide, herbicide, etc. Such coatings have generally been of a water soluble material, so that the coating would dissolve to allow exposure of the seeds to the atmosphere for development. Such water soluble materials include water soluble polymers. Specifically, U.S. Pat. No. 2,651,883 relates to use of polymeric water soluble polyelectrolytes as seed coatings. U.S. Pat. Nos. 3,707,807 and 3,598,565 relate to use of water soluble neutralized copolymer of an $\alpha$, $\beta$-unsaturated monocarboylic acid and a lower alkyl acrylate and a crosslinked copolymer of vinyl acetate and a lower alkyl acrylate. In contrast, U.S. Pat. No. 3,316,676 relates to a water insoluble seed coating, the integrity of which is destroyed by shrinkage due to contact with water. U.S. Pat. No. 3,905,152 relates to seeds having a coating thereon comprising non-porous, hydrophobic, non-phytotoxic particles which are adhered to each other and to the seeds by means of a hydrophilic binder in such a manner that the coating is highly porous and provides facile gas and water exchange between the seed and the environment.

SUMMARY OF THE INVENTION

According to this invention, seeds coated with compositions comprising a water insoluble but water sensitive polyelectrolyte complex are provided. The polyelectrolyte complex is functional in that it provides protection for the seeds from mechanical and environmental damage and may be used as a carrier for materials such as fertilizers, herbicides, pesticides, etc. An important feature, however, is the fact that the polyelectrolyte complex does not dissolve when contacted with water. Instead, it swells and falls away, thereby dissrupting the coating, and the swelling and falling away continue until the coating is removed. An advantage of such a coating is that there is no dissolved material available to fill the pores of the seeds to thereby retard germination. The coating quickly disintegrates upon contact with water for releasing any carried substances and expose the seeds to their natural environment.

BRIEF DESCRIPTION OF THE DRAWINGS

The drawings illustrate a preferred method and apparatus for coating seeds in accordance with this invention. In the drawings.

Figures 1, 2, 3:
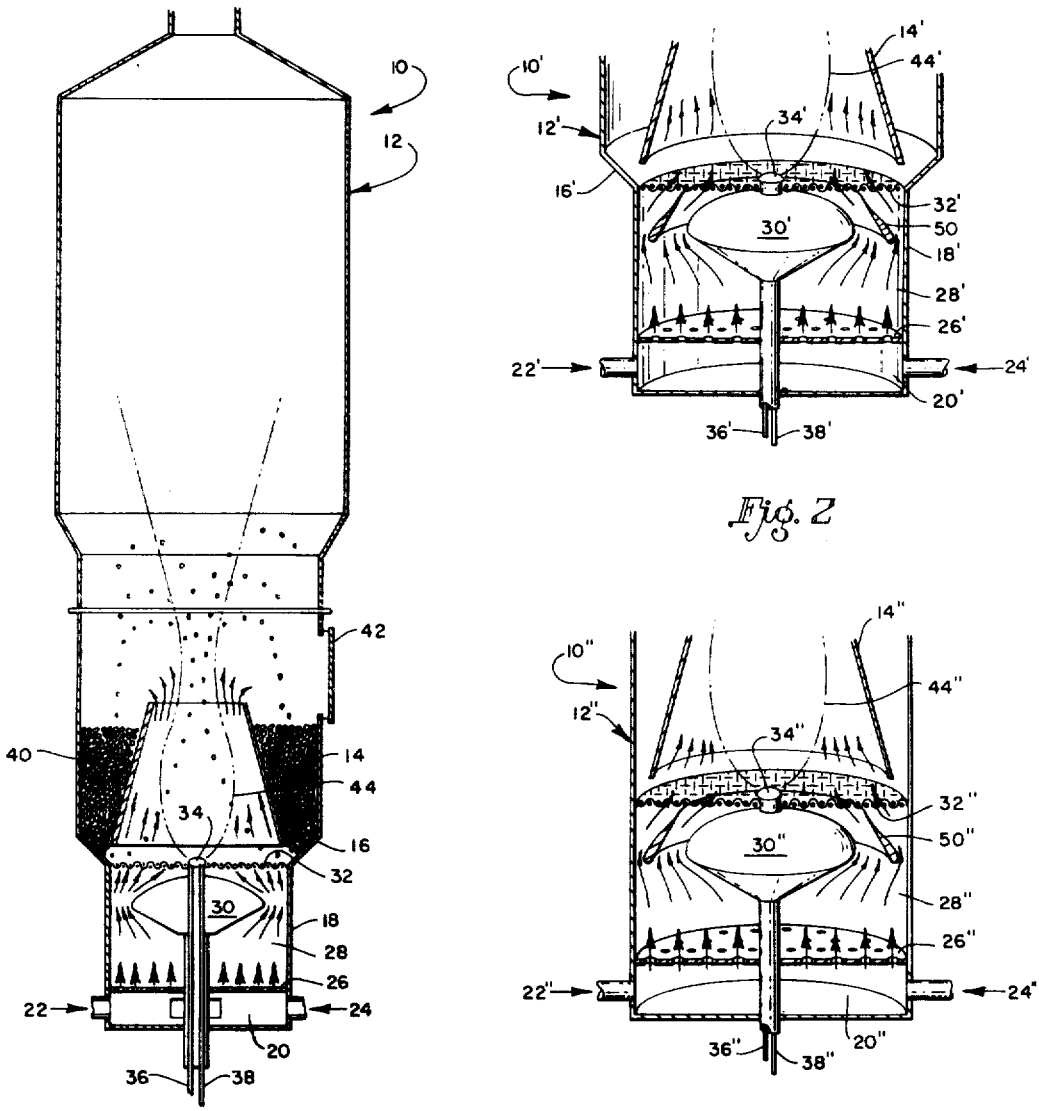
FIG. 1 is an elevation view in cross-section illustrating apparatus and showing gas flows and seed flow path from an annular bed through a truncated hollow cone and in return to the annular bed.
FIG. 2 is a partial elevation view in cross-section of a modified apparatus and illustrating the addition of an annular airfoil and showing the flow of gases relative to the aerodynamic structure and annular airfoil.
FIG. 3 is a partial elevation view in cross-section of another modified apparatus similar in all other respects to the modification shown in FIG. 2 except that the cross-section of the apparatus below the coating chamber is of the same diameter as that of the coating chamber;

FIG. 4 is a partial elevation view in cross-section of the upper portion of the apparatus, illustrating one possible manner of collecting the seeds by use of an air porous bag; and FIG. 5 is a graphic illustration of the height, thickness and angular relationships of the annular airfoil with respect to the aerodynamic structure, and the height above ($h_a$) and height below ($h_b$) relationships of the aerodynamic structure to the greatest cross-sectional diameter of the aerodynamic structure.

DETAILED DESCRIPTION OF THE INVENTION

In accordance with this invention, seeds are coated with polyelectrolyte complexes which are insoluble in polar organic solvents and water, but are capable of being swollen in these solvents to permit germination of plant seeds such as vegetables, crops, flowers, etc.

Polyelectrolyte complexes are known in the art. See, for example, KIRK OTHMER, Encyclopedia of Chemical Technology, 16, pp 117-133, and U.S. Pat. Nos. 2,832,746 and 2,832,747. Such polyelectrolyte complexes are ionically crosslinked hydrogels formed by combining a solution of an acidic polymeric substance with a solution of a basic polymeric substance. The polymers precipitate to form water-swellable gels having a wide range of properties dependent on the nature of the original polymers. Either the acidic polymer or basic polymer may be a copolymer wherein the comonomer or monomers can, for instance, engender the final polymer with modified water sensitivity, contribute to softening point, provide elastomeric properties, provide additional functionality, etc. The range of adjustment of the individual copolymer is understood by those skilled in the art of polymerization. A particularly valuable means of adjusting the properties of the final polyelectrolyte complex is the selection and relative concentration of acidic and basic functionality associated with homopolymers and copolymers. The acidic moiety can be as weakly acidic as a phenolic group or as strongly acidic as a sulfate or sulfonate group. Preferred acidic groups include the carboxyl group. Preferred basic groups include those containing primary, secondary or tertiary aliphatic or aromatic amino groups.

Polyelectrolyte complexes of interest in this invention are those which form an abrasion resistant coating on seeds, which allow water to permeate the coating to the seed, and which lose their integrity when contacted with water at least to a point which allows the seeds to germinate without inhibiting this natural process. Polyelectrolyte complexes meeting these criteria include those in which the ionic bonding between the acidic and basic polymers or polyelectrolytes is weakened by contact with water to the point that natural germination proceeds uninhibited.

Suitable acidic polymers or polyelectrolytes include natural and synthetic polymers which contain more than about 5 parts by weight of carboxylic, sulfuric, sulfonic, phosphoric, or phosphonic acid moiety per 1000 parts of polymer and the ionizable salts of such acidic moieties attached to natural and synthetic polymers such as polyacrylic acid, copolymer of maleic acid and styrene, sulfonated polystyrene, sulfonated lignin and soluble polypeptides having isoelectric points in the range of pH 2–5.

Suitable basic polymers of polyelectrolytes include natural and synthetic polymers which contains more than about 2 parts by weight of basic amino nitrogen per 1000 parts of polymer and the ionizable salts and quartenary ammonium complexes of such basic amino nitrogens such as poly-N,N-diethyl aminoethyl acrylate, poly-2-methyl-5-vinylpyridine, cellulose propionate morpholino butyrate, and polypeptides having an isoelectric point greater than about 7.

The acidic and basic polymers may be mixed in such quantities that the resulting polyelectrolyte complex has a pH range of from about 5–8. When a polyelectrolyte complex is made with either excess acid or excess base the excess functionality can be used to incorporate or attach other acidic or basic substances of value to the seed. For instance, a seed coating composed of a layer of polyelectrolyte complex made from 30 percent polyacrylic acid and 70 percent poly-2-methyl-5-vinylpyridine will have excess aromatic amine base functionality. This excess base can be neutralized with acidic substances of potential value to the plant such as gibberellic acid, indoleacetic acid, or nitrate ion. Conversely, the polyelectrolyte complex may contain excess acidic functionality and therefore also bind basic substances such as kinetin. Furthermore, the seed coating may contain more than one layer and each layer can be of a polyelectrolyte complex of different degrees of neutralization of the acidic and basic polymers. Such a seed coating may therefore serve as a controlled release layer for both acidic and basic substances of value to the seed, seedling, or seed bed wherein the active substances are weakly bound in the vicinity of the planted seed by ionic forces readily destroyed by the ion exchange mechanisms existing in the soil/seed interface.

Both the polymeric base or the polymeric acid may be compounded by techniques well known to the art of polymer technology with particulate substances or plasticizer-like substances for the purpose of modifying the polymeric properties and/or providing other substances of value to the seed, seedling, or seed bed. This method of adding substances is regarded as a mechanical inclusion of these substances within the polymeric matrix of the polyelectrolyte complex.

The coatings of polyelectrolyte complexes are formed on the seed by various techniques. One method is to contact the seed surface simultaneously with atomized droplets of solutions of the basic polymer and the acidic polymer. Solvents for both the polymers are well known by those skilled in the art. Normally, the coating will be applied to a thickness of between about 0.5 and 10 mils, or such as to result in a coating weight of from about 0.25% to about 5% based on the weight of the coated seed.

Another method is to alternately apply very thin layers of the basic polymer and the acidic polymer. In this instance only the interface between the layers is designated as polyelectrolyte complexes at the time the coating is applied. However, because of the nature of these water-sensitive polymers the action of the total coated layer is that of a true polyelectrolyte complex because as the water necessary to germinate the seed becomes available the coated layers swell but as they swell the acidic and basic macromolecules become mobile and react with each other to form a complete polyelectrolyte complex.

Active ingredient substances attached to either or both the acidic polymer and the basic polymer by ionic bonding are released as the bonding sites become involved in the more stable polyelectrolyte complex-type bond.

Still another method of practicing the invention consists of forming the polyelectrolyte complex and combining the complex with one or more active substances such as growth promoting hormones, micronutrients, fungicides, etc. The complex is then dried and pulverized to give an ionically cross-linked water-swellable particle which can be incorporated into a continuous matrix polymeric coating including another or the same polyelectrolyte complex as composes the particle but wherein the continuous matrix polymer is formed as a coating layer on the surface of the seed.

The nature of the polyelectrolyte complex makes it particularly suitable for use in forming pellets containing seeds. The advantages of pelleted seeds are known to the art. In such an application, a seed is contacted with particulate material such as clay, vermiculite, wood waste such as sawdust, ground corn cobs, ground hay and the like and at the same time with acidic and basic polymers which form polyelectrolyte complexes. The formation of the complex between the seed surface and various particles serves to adhere the particles to the seed and to each other. The advantage of forming an adhesive bond by this technique is that the adhesive bond is formed in the presence of water and the establishment of an oxygen and water permeable matrix of particles results. Also, the adhesive bond is formed very rapidly.

A preferred method and apparatus for application of the coating is illustrated in the drawings.

The apparatus employs a truncated hollow cone in which the slope or pitch of the walls is such that the seeds are accelerated at an increasing rate and not just at a rate so as to maintain the gas velocity at any given point in the cone at a level greater than that necessary to move the particles in a continuous upward direction. The significance of the slope or pitch of the truncated hollow cone of the invention is that when a particle first enters the cone at one rate of speed, it is then accelerated to a different rate of speed and continues to be accelerated to still different rates of speed as it moves upwardly through the cone. In this manner a separation is brought about between the particles so that after they are coated they may become sufficiently dry before coming into contact with other particles and thereby avoid undesirable clumping or agglomerating together. The pitch of slope is such as to cause a compression of the gas molecules and thereby cause the acceleration at an increasing rate.

In reference to FIG. 1, the coating apparatus is designated in general at 10 and includes a vertically disposed first hollow column 12 of regular shape. By "regular shape" is meant that it may be cylindrical, octagonal, hexagonal or of other configurations, so long as the hollow column is generally symmetrical with respect to its central axis. The hollow column contains therewithin the particle storage, coating, drying and deceleration zones, which will be described herein.

A truncated hollow cone 14, which may also be a tapered octagon or other tapered polygonal configuration, in other words, generally cone-shaped configurations, serving as an enclosure in which the upwardly flowing gases are received, compressed and accelerated, is centrally disposed within the first hollow column, has a uniformly decreasing cross-section in the upward direction and is of predetermined height dependent upon the size and weight of the seeds to be treated. Within the truncated hollow cone in ascending order are the coating and drying zones. The cone serves also to separate the coating and drying zones from the deceleration zone, which lies in the region above the upper end of the cone, and from the storage zones, which lies therebetween the cone and the interior wall surface of the first hollow column.

The first hollow column 12 is provided at its lower end with an inwardly tapered base 16. The lower end of the truncated hollow cone is spaced radially inwardly from the inwardly tapered base.

A second vertically disposed hollow column 18 of regular shape is connected to the inwardly tapered base of the lower end of the first hollow column, the wall surface of the inwardly tapered base forms a juncture with the wall surface of the second hollow column.

Disposed within the second hollow column is a first plenum chamber 20 into which a suitable compressed gas, such as air, may be provided through two or more opposed inlets 22, 24; a gas or air collimating plate 26; a second plenum chamber 28 separated from the first plenum chamber 20 by the collimating plate 26; at least one gas shaping or aerodynamic structure 30 disposed within the second plenum chamber; and a seed support or supporting screen 32, which extends across the second hollow column and is located above the aerodynamic structure.

The gas or air collimating plate 26 is a perforated plate which causes the gas or air in the first plenum chamber to pass into the second plenum chamber in an essentially vertical and uniform flow, as illustrated by the vertical arrows.

The gas shaping or aerodynamic structure 30 in cooperation with the adjacent wall surface of the second hollow column, compresses and focuses the upwardly moving gas or air flow so that it flows over a portion of the surface of the aerodynamic structure, upwardly through the particle support screen and into the entrance end of the truncated hollow cone. The flow upwardly around the aerodynamic structure constitutes an annular flow, which adheres to the surface of the aerodynamic structure in the nature of a Coanda flow.

A spray nozzle 34 preferably extends above the top of the aerodynamic structure 30 through which is sprayed a suitable coating material. It is more convenient to have the spray nozzle located at the top of the centrally disposed aerodynamic structure. The coating material is supplied from a suitable source (not shown) through a conduit 36 extending up through the aerodynamic structure, and an atomizing gas may be supplied from a suitable source (not shown) through a conduit 38, also extending up through the aerodynamic structure, for subsequent mixing at the nozzle. The spray nozzle may also be pressure-operated rather than gas-operated.

The upper surface of the gas shaping or aerodynamic structure is centrally disposed within and extends generally horizontally across the cross-section of the vertically disposed hollow column. In other words, it has a cross-sectional plane generally perpendicular to the vertical axis of the vertically disposed hollow columns. The outer edge of the upper surface is equally spaced from the wall surface of the hollow column and defines therebetween with the wall surface of the hollow column a reduced pressure region for acceleration in velocity of the upwardly flowing gases in such manner that the upwardly flowing gases form a boundary layer that is directed away from the wall surface of the hollow column and that adheres to the upper surface of the gas shaping or aerodynamic structure for flow across a portion thereof.

The upper surface of the aerodynamic structure may be flat (not illustrated), but is preferably curved or approximately spherical as illustrated. It may have a height ($h_a$) above the cross-sectional plane (See FIG. 5), therefore, of from about 0% to about 150%, or preferably from about 10% to about 150% of the greatest cross-sectional diameter (D) (See FIG. 5) of the aerodynamic structure.

The surface below the greatest cross-sectional diameter may also be flat (not illustrated) and may therefore have a depth or height ($h_b$) below of from about 0% to about 200% of the greatest cross-sectional diameter (D) (See FIG. 5). Preferably, the surface below is formed in the manner disclosed in the drawings.

The aerodynamic structure as disclosed and as described is thus adapted to compress and accelerate the flowing gases near the periphery of the hollow column and direct them toward the center of the hollow column at an angle from about 10° to about 45° from a direction parallel to the flowing gases from the gas or air plenums.

The truncated hollow cone defines at its lower end a large diameter somewhat smaller than the diameter of the vertically disposed first hollow column, and has an increased diameter from about 0% to about 25% greater than that of the plane of the particle support screen. The lower end of the truncated hollow cone is spaced a predetermined amount from the screen and the upper end defines a diameter of from about 20% to about 80% of that of the lower end. The height of the cone ranges from about one to about six times the diameter of the lower end.

In operation, seeds 40 may be suitably loaded into the coating apparatus 10, as through a closable opening at 42, into the storage zone lying between the wall surface of the first hollow column 12 and the outside wall surface of the truncated hollow cone 14. The seeds are thus situated in an annular bed around the truncated hollow cone 14. The sloping outer wall surface of the truncated hollow cone, the inwardly sloping tapered base 16 of the first hollow column and the screen 32 serve to contain the particles in the annular bed prior to starting-up the coating operation.

The gas or air is turned on to start the circulation of the seeds from the annular bed or storage zone into the coating, drying and deceleration zones and in return to the upper portion of the annular bed. The atomizing spray is then turned on and appropriately adjusted in a suitable manner by controls (not shown).

As previously pointed out, the Coanda flow or effect is named for the tendency of a fluid, either gaseous or liquid, to cling to a surface that is near an orifice from which the fluid emerges. Such "orifice" in this instance is formed in the region therebetween the closest approach of the aerodynamic structure to the adjacent side wall surface. The gas flow emerging from the "orifice" region around the aerodynamic structure is an annular flow which clings or adheres to the surface of the aerodynamic structure. The flow, therefore, from any one selected location around the "orifice" is opposed by the other flows so that it is prevented from continuing further over the upper surface of the aerodynamic structure by being forced upwardly away from the upper surface at some point for flow into the truncated hollow cone. A partial vacuum is formed in the region just above the upper surface of the aerodynamic structure and at the lower edge of the truncated hollow cone and this aids in the compression and focusing of the rising annular flow of gases. The upward flow is consequently caused to have a conical shape, as seen in phantom lines in FIG. 1 at 44 within the cone, and has a centering effect on the particle impelled upwardly through the cone.

As also pointed out, an important part of the Coanda effect is the tendency of the flow or gas or liquid to entrain, or draw in, more gas or liquid from the surrounding environment. In this latter manner, the particles are pulled from the annular bed or storage zone into the upwardly flowing gas due to the aforementioned partial vacuum or reduced pressure region that exists just above the screen adjacent the path of upward flow as a consequence of this Coanda effect. This reduced pressure or partial vacuum is directed perpendicular to the annular airflow from the "orifice". It is a different effect, however, from the horizontal shunting action occurring in the Wurster et al apparatus described above because there the horizontal shunting would extend not only toward the axis of the apparatus but also inefficiently toward the outer wall surface of the coating apparatus.

Once the seeds are pulled into the upwardly flowing gas within the truncated hollow cone, they are impelled upwardly in an accelerating gas or air stream. As the seeds pass through the lower central region or coating zone within the cone, they are contacted with an atomized spray coating of material. This atomized spray emerges from the spray nozzle 34 because the liquid coating substance is either forced through a single orifice designed to convert bulk liquids into droplets, or the liquid and an atomizing air stream emerge simultaneously from jets adjacent to each other. In either case, the fine droplets of coating material are in a flowable state, because the material is dissolved or melted in the region immediately above the spray nozzle.

Further up the truncated hollow cone, the liquid nature of the coating material, as deposited on the seeds, changes to solid by evaporative or other solidification processes. During the transition from liquid to solid, the seeds pass through a stage when they are sticky or tacky and would agglomerate if they contacted each other. This contact is prevented by the slope or pitch of the walls of the truncated hollow cone and consequent accelerating boost of the seeds to separate them in the manner previously discussed.

The conical nature of the cone causes a compression and acceleration of the rising column of gases and the upward velocity or acceleration of the particles occurs at an increasing rate as they rise in the cone. This acceleration causes an increasing vertical separation in space between the seeds and therefore reduces the tendency for the particles to contact each other until the coating has become nontacky. It is this region of the cone that is thus called the "drying zone".

When the compressed gases and entrained seeds pass upwardly out of the upper end of the cone, they expand into the larger area of the upper portion of the first hollow column and thus decelerate to a velocity too low to suspend the seeds. This is the deceleration zone, where further drying takes place, and the seeds then fall by gravity action to the annular bed where they gradually move down, also due to gravity, until they are pulled into the coating zone again. This recycling or recirculation continues until, based on previous experiments, a sufficient coating has been applied.

The atomized spray is turned off, and the gas or air entraining flow may be shut down or may be increased to drive the coated seeds into the uppermost region of the first hollow column, as for collection in the manner illustrated in FIG. 4. Any other suitable manner of unloading the finally coated particles may also be used.

A coating apparatus having the design characteristics essentially as shown in FIG. 1, and having a diameter of eight (8) inches across the lower end and four (4) inches across the upper end of the truncated hollow cone, is charged with twenty-five (25) pounds of cotton seeds. About 250 standard cubic feed per minute of air at about 7 p.s.i.g. is admitted to the plenum chamber 20. This air causes a circulation of pellets through the truncated hollow cone 14, and the height of the cone above the support screen 32 is adjusted to obtain a pellet flow rate such that all the pellets in the annular storage zone move through the cone about once every minute. A coating latex is pumped through the spray nozzle 34 at the same time as 5 SCFM of atomizing air at 40 p.s.i.g. is supplied to the nozzle. The pumping rate is adjusted to pump one (1) pound of solution per minute. The apparatus is operated for about 45 minutes. The product is a pellet core coated with about a 2-mil layer of the polymer.

If the gases flowing upwardly around the aerodynamic structure could be seen as a series of layers of molecules, merely for sake of discussion, it is thought that there is an insignificant flow of molecules or layer or so of molecules along the interior wall surface of the second hollow column. By "insignificant" is meant that such layer or layers of molecules will not perform any supporting function of the particles in the annular bed.

Moving, therefore, radially inwardly from the interior wall surface of the second hollow, the more significant layers of molecules are caused to bend toward the gas shaping or aerodynamic structure, the innermost adhering to the surface of that structure as they pass upwardly through the "orifice" region. This adherence of the molecules to the surface of the aerodynamic structure may be favorably compared to the "teapot effect", which is a low-speed form of the "Coanda effect". When water is poured slowly from a glass, it tends to stick to the side of the glass in the same way that tea sticks to the spout of a teapot. High speed fluids behave similarly and adhere to a surface of suitable shape.

As the rising molecules flow over the surface of the aerodynamic structure after having passed the "orifice" region, previously mentioned, at some point along the upper surface of the aerodynamic structure the opposing character of the annular flow forces the molecules upwardly away from the upper surface as well as the adjacent molecule layers. A partial vacuum is created above the aerodynamic structure due to the high speed upward flow of gases, causing an inward bending of the upwardly moving molecules.

In the apparatus herein described, the seeds move down in the annular bed by gravity without any "dancing" occurring, and are drawn into the upwardly flowing gases by the partial vacuum. Thus, any attrition that might occur is greatly minimized, and the overall operation is much more efficient.

In reference to FIG. 2 in which a modification is disclosed, the same reference numbers will be used to identify similar elements previously described, except that they will be primed to show that it is a different embodiment under discussion.

FIG. 2 represents an embodiment wherein the size of the coating apparatus 10' has been increased in order to handle larger batch loads of seeds for coating treatment. It has been found that it is more practical to add an additional gas shaping or aerodynamic structure or an annular airfoil 50 instead of increasing the size of the aerodynamic structure 30'. In this manner, larger amounts of upwardly flowing gas or air may be supplied undiminished or unobstructed by a larger aerodynamic structure, and the annular airfoil serves to supplement the compression and focusing action on the upward gas flows so that substantially all gas flows move through the truncated hollow cone 14'.

Additional or multiple gas shaping or annular airfoils (not shown) also may be used for still larger coating apparatus. The exact shape and placement of the airfoils are functions of a number of variables. The most significant of the variables are size of the apparatus, size of the seeds to be coated, density of the seeds, rate of gas or air flow and the rate of recirculation of the seeds through the coating zone desired.

In a larger-scale coating apparatus, therefore, one or more annularly shaped and placed gas shaping or aerodynamic structures or airfoils, angled or curved, may be provided concentric with and radially outwardly of the central gas shaping or aerodynamic structure. The annular airfoils may be attached to the central aerodynamic structure or to the walls of the coating apparatus by radial struts in such manner as to exert a minimum deflection of the upwardly flowing gases.

The annular aerodynamic structure is inwardly inclined in the upward direction so that its inclination lies in a plane extending about 10° to about 45°, as measured from the axis perpendicular to the diameter of the coating apparatus. The inwardly inclined annular structure provides a surface on which the gas or air impinges for subsequent shaping and direction upwardly into the truncated hollow cone.

The vertical height of the annular structure may be about 10–50% of the perpendicular cross section diameter of the coating apparatus.

In the reference to FIG. 5, when the annular gas shaping structure has the configuration of an airfoil having at least one curved surface extending generally in the direction of gas floww, the overall angle of a line described from a point $p_1$, on the lower rim of the airfoil to a point $p_2$, on the upper rim in the vertical direction, or perpendicular to a line which is tangent to the upper curved surface of the centrally disposed aerodynamic structure, is from about 10° to about 45° inward facing, as measured from the axis perpendicular to the diameter of the coating apparatus.

The cross-sectional configuration of an annular airfoil in a plane described from the center of the cross sectional area of the coating apparatus to a point, $p_1$, on the lower rim of the airfoil to a point, $p_2$, in the upper rim of the airfoil is teardrop, or similar to the crosssectional shape of a lifting aerodynamic shape, and having the thicker cross section on the forward part with reference to the direction facing the upwardly flowing gases. The thickest part is located about two-fifths (2/5) to about one-half (½) of the height in the vertical direction. In other words, the height (H) of the thickest part (T), or HT is equal to about 2/5 H to about ½ H. The thickest cross section (T) is from about one-sixth (1/6) to about two-fifths (2/5) of the height (H) of the airfoil; or T is equal to about 1/6 H to about 2/5 H.

The size, placement and geometrical configuration of the annular gas shaping structure are such, therefore, that the upwardly flowing gases are deflected radially inwardly at an angle from about 10° to about 45° from a direction parallel to the original gas flow.

In reference to FIG. 3, the same reference numbers will be used to identify similar elements previously described, except that they will be double-primed to show that it is still another different embodiment under discussion.

FIG. 3 represents an embodiment wherein the size of the coating apparatus 10" has been increased to the same extent as that disclosed in the FIG. 2 embodiment. The embodiment in FIG. 3 differs from the embodiment in FIG. 2 in that the first and second hollow columns are disclosed as being co-extensive in cross-sectional diameter. In other words, the coating apparatus is disposed within a single hollow column. It could also be of smaller size so that only one gas shaping or aerodynamic structure 30" is employed as in FIG. 1, instead of a size requiring the annular airfoil 50".

The recycling or recirculation in this embodiment is necessarily faster because the seeds are not as readily restrained in the annular bed region as they would be if there were an inwardly tapered base to assist in such restraint. Proportionately smaller batch loads may be used, therefore, since the recirculation of the seeds is substantially continuous with the particles spending very little time in the annular bed. For this reason, an embodiment of this character is suitable for special purposes, while the embodiments of FIG. 1 and FIG. 2 are deemed to be of more general use.

Figure 4:
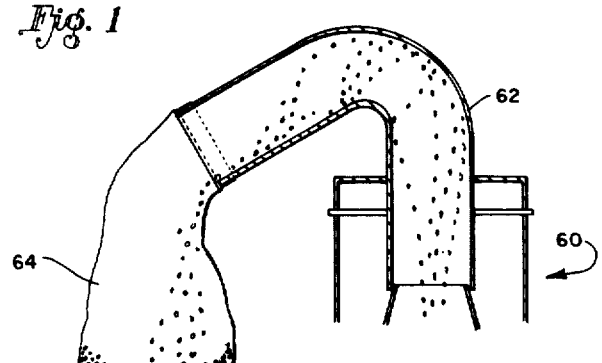

In FIG. 4 this embodiment represents one manner of unloading a coating apparatus, and was briefly mentioned above with respect to one possible operation of the embodiment of FIG. 1.

Only the upper portion of a coating apparatus 60 is shown, and it could be used for any of the previously described embodiments. A conduit 62 is installed within the upper portion of the apparatus, as shown, and a gas or air porous collection bag 64 may be installed at the remote end of the conduit for collecting the finally coated seeds in the manner already heretofore described.

In any of the embodiments described above, the truncated hollow cones may be adapted to be adjusted for movement upwardly or downwardly in a vertical plane. The same may also be accomplished with the aerodynamic structure, the annular airfoils and the spray nozzles, as desired to suit gas or air flows, seed sizes and weights, coating material consistencies and whatever other controlling factors may be concerned.

The seeds to be coated may be batch-loaded and treated; or, if deemed advantageous, two or more such coating apparatus may be arranged in cascaded manner to provide for a continuous coating operation. The inlet for the seeds in a cascaded arrangement may be disposed above the annular storage of one apparatus and the particles metered in predetermined manner into the annular storage bed, while the outlet to the next coating apparatus may be disposed on the opposite side of the annular storage bed and constitute a weir for outflow of excess coated particles. The inlet may also be disposed for gravity flow of seeds to or into the annular storage bed. It may be desirable to provide for different coatings in different apparatus, or provide supplemental coatings.

Multiple spray nozzles may also be employed, as desired, to achieve different coating effects.

The following examples are submitted for a better understanding of the invention.

EXAMPLE 1

Soybean seeds are coated by simultaneously contacting the seed surface with air-atomized sprays of acidic polymer and basic polymers dissolved in suitable solvents. In this example, the acidic polymer is polyacrylic acid as a 5% solids solution in ethanol. The basic polymer is a copolymer containing 85% 2-methyl-5-vinylpyridine and 15% styrene and the solvent is acetone. The seeds are suspended in a stream of air heated to 50° C. and the solutions are sprayed onto the seed at a rate that the seeds are never observably wet with the solutions. At the instant of contact of the solutions the acidic polymer reacts with the basic polymer to form an ionically cross-linked polymeric layer on the seed. This layer is insoluble in polar organic solvents and water but is swollen by these solvents. The seeds are contacted with water and air at 70° F. for 7 days. Uncoated control seeds are also contacted with water under the same conditions. After 24 hours, both the coated seeds and the control seeds are fully imbibed with water. After 48 hours, both coated and uncoated seeds have emergent radicals which have essentially the same average length. After 4 days, both the control and coated seeds have the same degree of development of hypocotyl. It is concluded that the coating does not interfere with the natural processes of seed germination.

EXAMPLE 2

The above coating was repeated except that the acidic polymer solution also contains 4% Captan fungicide, N-(trichloromethylthio)-4-cyclohexene-1,2-dicarboximide, based on the combined weight of the acidic and basic polymer. The seeds are contacted with water as before but also with fungi spore contaminated ground corn. These seeds germinated normally in the presence of actively growing fungi.

EXAMPLE 3

Cotton seeds are coated in an air suspension type coater with a coating comprised of a polyelectrolyte complex wherein one air atomizing jet sprays the acidic polymer and another sprays the basic polymer. In this instance 250 g of cotton seeds are placed in the air suspension coater and are circulated through the coating zone with air heated to 50° C. After the seeds are circulating properly two air atomized jets are started. From one jet a 8% solids solution of the 1:1 copolymer of maleic anhydride and styrene having an intrinsic viscosity of 0.75 and dissolved in acetone is caused to contact the seeds. Simultaneously from the other jet is sprayed a 10% solution of poly-2-methyl-5-vinylpyridine, having an intrinsic viscosity of 0.65, dissolved in 90% acetone and 10% water. As the two solutions contact each other on the surface of the seed two chemical reactions take place. First, a significant portion of the anhydride moieties react with water to form a 2-carboxylic acid group. Second, the newly formed carboxyl groups react with the basic amino nitrogen to form a polyelectrolyte complex. The seeds are considered to be adequately coated when the layer on the seeds is about 5 mils thick. The coated cotton seeds are tested for imbibition and germination by placing the seeds between moistured towels. The seeds become fully imbibed with water in about 22 hours and germination is determined to be normal in 4 days.

EXAMPLE 4

Soybean seeds are coated by the same procedure as in Example 1. The same polymers are used. In the instance, however, based on the weight of the soybeans 12 ppm of gibberellic acid is added to the solution containing poly-2-methyl-5-vinylpyridine. Since gibberellic acid is a carboxylic acid it forms a weak salt binding with the basic amino groups. This binding and the limited swelling inherent of a polyelectrolyte complex causes the gibberellic acid to become available to germinating seed over a controlled time base. The soybean seeds germinate and emerge from the seed bed 36 hours before untreated seeds. The resultant plants continue to respond to the gibberillic acids via the slow leaching of the polyelectrolyte complex remaining in the vicinity of the newly formed roots. To measure the duration of the gibberellic acid affect a coated seed and an uncoated seed are planted within one half of each other and one inch below the soil surface. The coated seed shows the effect of the intimate contact of the gibberellic acid by germinating first and showing greater elongation initially. However, after germination and initial root formation the uncoated seed also takes up giberellic acid from the remains of the seed coating of the coated seed and now also shows accelerated elongation as compared to uncoated seeds plant at a point distant from the coated seed.

EXAMPLE 5

Cellulose propionate morpholino butyrate containing 2.25% basic amino nitrogen groups is dissolved in acetone to give a 6% solids solution. Based on the polymer, 300 ppm of 1 naphthaleneacetic acid is added. This solution is designated as the basic polymer solution. An acidic polymer solution consists of polymethacrylic acid dissolved in acetone at the level of 5% solids. Grain sorghum seeds are placed in an air suspension coater equipped with two air atomizing jets. The machine is started using air heated to 50° C. As soon as the seeds are circulating properly the basic solution is sprayed onto the seeds from one jet and the acidic solution is sprayed onto the seed from the other jet. As the solutions contact the seed and spread over the surface due to impact they become mixed and interact to form a polyelectrolyte complex. The coating is applied until the seeds are covered with a 3 mil layers. The coated seeds are planted one inch deep in typical agriculturally suitable sandy loom soil having a water tension of 1.5 hrs. and an average temperature at the planted depth of 23° C. Germination requires only 3.5 days whereas an uncoated control requires more than 5 days. Furthermore, the coated seeds show very uniform emergence requiring only about 12 hours for the time for first emergence to the last is emerged. The control seeds require 3 days 90% of total emergence from the time of first emergence and a few seeds are still in the process of emergence 10 days after first emergence. Seeds coated with the same polyelectrolyte complex but not containing the germination promoting naphthaleneacetic acid germinate normally compared to uncoated seeds.

EXAMPLE 6

The experiment described in Example 5 is repeated except that 200 ppm of gibberellic acid based on the weight of basic polymer is used instead of the naphthaleneacetic acid. The results are similar to those of Example 2 except that the first emergence of the coated seeds is about 6 hrs. sooner than when naphthaleneacetic acid is used.

EXAMPLE 7

A copolymer having a composition of 20% by weight of acrylic acid and 80% 2-hydroxyethyl acrylate is dissolved in acetone to give a 6% solids solution. In another acetone solution a homopolymer of N,N-diethylaminoethyl acrylate is dissolved to give 10% solids. Into this solution is added 10 g of dilute nitric acid for each 10 g of amino polymer. These solutions are sprayed onto soybean seeds from separate jets in an air suspension coater to provide a layer of continuous film about 3 mils thick on the seeds. These seeds are tested for inhibition of water and germination and are found to respond at the same rate as an uncoated control.

EXAMPLE 8

Seeds are coated as described in Example 7 except that the acidic copolymer solution contains 0.001 g of kinetin (plant hormone) for each 10 g of polymer and the amine-containing polymer solution contains 0.001 g of gibberellic (plant hormone) acid for each 10 g of polymer. The coated seeds obtained with about 3 mil thick coating layers are germinated and compared to uncoated seeds and to coated seeds obtained by the process of Example 7. These seeds germinate about 36 hours before the control seeds or the coated seeds without the plant hormones.

It will be obvious to those skilled in the art that in addition to substances beneficial to healthy seed germination and growth such as fungicides, herbicides, pesticides, fertilizers, growth promoters, hormones, etc., various additives such as fillers, pigments, dyes, etc., may be added to the coating compositions.

Unless otherwise specified, all parts, percentages, ratios, etc., are by weight.

The invention has been described in detail with particular reference to certain preferred embodiments thereof, but it will be understood that variations and modifications can be effected within the spirit and scope of the invention.

I claim:

1. A plant seed having a substantially continuous coating on the surface thereof, said coating comprising a polyelectrolyte complex of an acidic polymer and basic polymer, said polyelectrolyte complex being water insoluble, but adapted to swell and disintegrate when in contact with water.

2. A plant seed according to claim 1 wherein said acidic polymer contains at least one carboxyl group.

3. A plant seed according to claim 1 wherein said basic polymer contains an amino group.

4. A plant seed according to claim 1 wherein said acidic polymer contains at least one carboxyl group and said basic polymer contains at least one amino group.

5. A plant seed according to claim 1 wherein said acidic polymer contains at least 5 parts by weight of a carboxylic, sulfuric, sulfonic, phosphoric or phosphonic acid moiety or ionizable salt thereof per 1000 parts of polymer.

6. A plant seed according to claim 1 wherein said basic polymer contains at least 2 parts by weight of a basic amino nitrogen per 1000 parts of said polymer.

7. A plant seed according to claim 1 wherein said basic polymer contains at least 2 parts by weight of ionizable salts or quaternary ammonium complexes of basic amino nitrogen per 1000 parts of said polymer.

8. A plant seed according to claim 1 wherein the polyelectrolyte complex resulting from the combination of said acidic and basic polymers has a pH of from about 5 to about 8.

9. A plant seed according to claim 1 wherein said basic polymer is selected from poly N,N-diethyl aminoethyl acrylate, poly-2-methyl-5-vinylpyridine, cellulose propionate morpholino butyrate and polypeptides having an isoelectric point greater than about 17.

10. A plant seed according to claim 1 wherein said coating contains at least one substance selected from the group consisting of fungicides, bactericides, herbicides, pesticides, fertilizers, growth promoters and hormones.

11. The method of treating plant seeds which comprises applying as a coating to the seeds a polyelectrolyte complex of an acidic polymer and basic polymer, said polyelectrolyte complex being water insoluble, but adapted to swell and disintegrate when in contact with water.

12. The method of claim 11 wherein said coating has a thickness of between about 0.5 to about 10 mils.

13. The method of claim 11 wherein said coating contains a substance which is beneficial to said seeds.

* * * * *